(12) United States Patent
Catt et al.

(10) Patent No.: US 10,182,748 B2
(45) Date of Patent: Jan. 22, 2019

(54) SYSTEM FOR THE SELF-MONITORING AND REGULATION OF BLOOD GLUCOSE

(75) Inventors: Michael Catt, Newcastle upon Tyne (GB); Michael Trenell, Newcastle upon Tyne (GB)

(73) Assignee: University of Newcastle Upon Tyne, Newcastle upon Tyne (GB)

( * ) Notice: Subject to any disclaimer, the term of this patent is extended or adjusted under 35 U.S.C. 154(b) by 481 days.

(21) Appl. No.: 14/002,341

(22) PCT Filed: Mar. 19, 2012

(86) PCT No.: PCT/GB2012/050595
§ 371 (c)(1),
(2), (4) Date: Sep. 20, 2013

(87) PCT Pub. No.: WO2012/123765
PCT Pub. Date: Sep. 20, 2012

(65) Prior Publication Data
US 2014/0005499 A1    Jan. 2, 2014

(30) Foreign Application Priority Data

Mar. 17, 2011 (GB) .................................. 1104513.5
Jun. 30, 2011 (GB) .................................. 1111126.7

(51) Int. Cl.
*A61B 5/145* (2006.01)
*A61B 5/11* (2006.01)
(Continued)

(52) U.S. Cl.
CPC ........ *A61B 5/14532* (2013.01); *A61B 5/0022* (2013.01); *A61B 5/01* (2013.01);
(Continued)

(58) Field of Classification Search
CPC ................................................ A61B 5/14532
(Continued)

(56) References Cited

U.S. PATENT DOCUMENTS

2003/0208110 A1* 11/2003 Mault ................. A61B 5/0002
600/300
2003/0208113 A1* 11/2003 Mault ................ A61B 5/14532
600/316
(Continued)

FOREIGN PATENT DOCUMENTS

DE    20 2007 010056 U1    9/2007
WO    WO-2010/022387 A1    2/2010
WO    WO 2010108287 A1 *  9/2010    ........... A61B 5/1117

OTHER PUBLICATIONS

American College of Sports Medicine & American Diabetes Association; "Exercise and Type 2 Diabetes"; Medicine & Science in Sports & Exercise, vol. 42, No. 12; Dec. 2010; pp. 2282-2303.
(Continued)

*Primary Examiner* — Carl H Layno
*Assistant Examiner* — Dacheng Xie
(74) *Attorney, Agent, or Firm* — Winstead PC

(57) ABSTRACT

The present invention relates to a self monitoring device for attachment to the body, which incorporates real-time and correlated measurement of body movement and physiological analytes of metabolism (e.g. glucose) that can be modulated by physical activity. The system enables real time and personalized modulation of the selected physiological analyte(s) through appropriately selected cued activities and other evidence based clinical guidance dependent on previous and current analyte levels correlated with previous and current patterns of movement. The system also allows for personalization of the outputs with regular calibration to the user.

22 Claims, 7 Drawing Sheets

(51) Int. Cl.
     A61B 5/00      (2006.01)
     A61B 5/01      (2006.01)
     A61B 5/053     (2006.01)
     A61B 5/1459    (2006.01)
     G06F 19/00     (2018.01)
     G16H 50/20     (2018.01)

(52) U.S. Cl.
     CPC .......... *A61B 5/0531* (2013.01); *A61B 5/1112*
          (2013.01); *A61B 5/1118* (2013.01); *A61B*
          *5/1459* (2013.01); *A61B 5/14503* (2013.01);
          *A61B 5/7246* (2013.01); *A61B 5/742*
          (2013.01); *A61B 5/7405* (2013.01); *A61B*
          *5/746* (2013.01); *A61B 5/7455* (2013.01);
          *G06F 19/00* (2013.01); *G06F 19/3481*
          (2013.01); *A61B 2562/028* (2013.01); *A61B*
          *2562/0219* (2013.01); *G06F 19/3456*
          (2013.01); *G16H 50/20* (2018.01)

(58) Field of Classification Search
     USPC ........ 600/300–301, 316, 317, 319, 348, 365
     See application file for complete search history.

(56)                References Cited

U.S. PATENT DOCUMENTS

| | | | | |
|---|---|---|---|---|
| 2009/0069787 | A1* | 3/2009 | Estes ................... | A61M 5/1413 604/503 |
| 2009/0177068 | A1* | 7/2009 | Stivoric ................... | A61B 5/01 600/365 |
| 2010/0176952 | A1* | 7/2010 | Bajcsy ...................... | A61B 5/11 340/573.1 |
| 2010/0318293 | A1* | 12/2010 | Brush ..................... | G01C 21/20 701/431 |
| 2011/0028818 | A1* | 2/2011 | Moberg ............ | A61M 5/14244 600/365 |
| 2011/0071765 | A1* | 3/2011 | Yodfat .............. | A61M 5/14248 702/19 |

OTHER PUBLICATIONS

Allen, Nancy A., et al.; "Continuous Glucose Monitoring in Non-Insulin-Using Individuals with Type 2 Diabetes: Acceptability, Feasibility, and Teaching Opportunities"; Diabetes Technology & Therapeutics, vol. 11, No. 3; Mar. 2009; pp. 151-158.
Allen, Nancy A., et al.; "Feasibility and Acceptability of Continuous Glucose Monitoring and Accelerometer Technology in Exercising Individuals with Type 2 Diabetes"; Journal of Clinical Nursing, vol. 18, No. 3; Jun. 11, 2008; pp. 373-383.
Ancoli-Israel, Sonia, et al.; "The Role of Actigraphy in the Study of Sleep and Circadian Rhythms"; Sleep, vol. 26, No. 3; Mar. 2003; pp. 342-392.
Battelino, Tadej, et al.; "Clinical Use of Real-Time Continuous Glucose Monitoring"; Current Diabetes Reviews, vol. 4, No. 3; Feb. 2008; pp. 218-222.
Berntsen, S., et al.; "Validity of Physical Activity Monitors in Adults Participating in Free-Living Activities"; Br J Sports Med, vol. 44; Jul. 15, 2008; pp. 657-664.
Bonomi, A.G., et al.; "Improving Assessment of Daily Energy Expenditure by Identifying Types of Physical Activity with a Single Accelerometer"; J Appl Physiol 107; Jun. 23, 2009; pp. 655-661.
Bruttomesso, Daniela, et al.; "Closed-Loop Artificial Pancreas using Subcutaneous Glucose Sensing and Insulin Delivery and a Model Predictive Control Algorithm: Preliminary Studies in Padova and Montpellier"; J Diabetes Sci Technol, vol. 3, Issue 5; Sep. 2009; pp. 1014-1021.
Buckingham, Bruce, et al.; "Prevention of Nocturnal Hypoglycemia using Predictive Alarm Algorithms and Insulin Pump Suspension"; Diabetes Care, vol. 33, No. 5; May 2010; pp. 1013-1017.

Carstensen, Bendix, et al.; "Measurement of Blood Glucose: Comparison between Different Types of Specimens"; Ann Clin Biochem, vol. 45; Mar. 2008; pp. 140-148.
Chillarón, Juan J., et al.; "Estimated Glucose Disposal Rate in Assessment of the Metabolic Syndrome and Microvascular Complications in Patients with Type 1 Diabetes"; J Clin Endocrinal Metab, vol. 94, No. 9; Jul. 7, 2009; pp. 3530-3534.
Clarke, William L., et al.; "Closed-Loop Artificial Pancreas using Subcutaneous Glucose Sensing and Insulin Delivery and a Model Predictive Control Algorithm: The Virginia Experience"; J Diabetes Sci Technol, vol. 3, Issue 5; Sep. 2009; pp. 1031-1038.
Colberg, Sheri R., et al.; "Exercise and Type 2 Diabetes"; Diabetes Care, vol. 33, No. 12; Dec. 2010; pp. 2692-2696.
Danne, T., et al.; "Reducing Glycaemic Variability in Type 1 Diabetes Self-Management with a Continuous Glucose Monitoring System based on Wired Enzyme Technology"; Diabetologia, vol. 52; Jun. 13, 2009; pp. 1496-1503.
Bourey, Raymond E., et al.; "Effect of Exercise on Glucose Disposal: Response to a Maximal Insulin Stimulus"; J Appl Physiol, vol. 69, No. 5; Jun. 1990; pp. 1689-1694.
Esliger, Dale W., et al.; "Validation of the GENEA Accelerometer"; Medicine & Science in Sports & Exercise; Jun. 14, 2010; 30 pages.
Abbott Diabetes Care Inc.; "Freestyle Lite"; https://www.myfreestyle.com/freestyle-lite-overview; Jun. 11, 2015; 8 pages.
Hansen, D., et al.; "Continuous Low-to Moderate-Intensity Exercise Training is as Effective as Moderate-to High-Intensity Exercise Training at Lowering Blood $HbA_{1c}$ in Obese Type 2 Diabetes Patients"; Diabetologia, vol. 52; Apr. 16, 2009; pp. 1789-1797.
Healy, Genevieve N., et al.; "Objectively Measured Light-Intensity Physical Activity is Independently Associated with 2-h Plasma Glucose"; Diabetes Care, vol. 30, No. 6; Jun. 2007; pp. 1384-1389.
Horowitz, Paul, et al.; "The Art of Electronics"; Cambridge University Press; 1980; pp. 1014-1016.
Hurling, Robert, et al.; "Using Internet and Mobile Phone Technology to Deliver an Automated Physical Activity Program: Randomized Controlled Trial"; J Med Internet Res., vol. 9, No. 2; Feb. 2007; 20 pages.
STMicroelectronics; "LIS331DLH"; Doc ID 15094 Rev 3; Jul. 2009; 38 pages.
Morgenthaler, Timothy I., et al.; "Practice Parameters for the Clinical Evaluation and Treatment of Circadian Rhythm Sleep Disorders"; Sleep, vol. 30, No. 11; Aug. 2007; pp. 1445-1459.
National Institute for Health and Clinical Excellence (NICE); "Type 2 Diabetes: The Management of Type 2 Diabetes"; Nice Clinical Guideline 66; May 2008; 44 pages.
Oliver, N. S., et al.; "Glucose Sensors: A Review of Current and Emerging Technology"; Diabetic Medicine, 26; Nov. 25, 2008; pp. 197-210.
Tsuchiya, Kazuyoshi, et al.; "Development of Blood Extraction System for Health Monitoring System"; Biomedical Microdevices 7:4; Dec. 2005; pp. 347-353.
Voon, Rudi, et al.; "The Use of an Energy Monitor in the Management of Diabetes: A Pilot Study"; Diabetes Technology & Therapeutics, vol. 11, No. 2; Feb. 2009; pp. 113-118.
Yokoyama, H., et al.; "Non-Oxidative Glucose Disposal is Reduced in Type 2 Diabetes, but can be Restored by Aerobic Exercise"; Diabetes, Obesity and Metabolism, vol. 10; Jan. 2007; pp. 400-407.
Abraham, Volkhard, "International Search Report for PCT/GB2012/050595," dated Jun. 14, 2012.
Abbott; https://www.diabetescare.abbott//index.html; Ver. 5.0; Nov. 2016; 4 pages.
Abbott Laboratories; "FreeStyle Navigator Continuous Glucose Monitoring System"; http://web.archive.org/web/20101216013517/http://freestylenavigator.com/index.htm; Dec. 16, 2010; 1 page.
Bodymedia, Inc.; "Introducing the BodyMedia SenseWear System"; http://web.archive.org/web/20101118052208/http://sensewear.bodymedia.com/; Nov. 18, 2010; 1 page.
Microchip Technology Inc.; http://www.microchip.com; 1998; 2 pages.
STMicroelectronics; http://www.st.com/content/st_com/en.html; as accessed on Feb. 14, 2017; 5 pages.

(56) References Cited

OTHER PUBLICATIONS

Touma, Carol, et al.; "Does Lack of Sleep Cause Diabetes?"; Cleveland Clinic Journal of Medicine, vol. 78, No. 8; Aug. 2011; pp. 549-558.
Bloomgarden, Zachary T., "Diabetes and Obesity," American Diabetes Association Annual Meeting, 1999; pp. 118-124.

* cited by examiner

Algorithm

A= Ideal glucose level

B= Current glucose level

C= Target glucose level (suggested or self identified)

D= Rate of change

E= Known rate of change for a specific activity (from calibration)

SYSTEM FOR THE SELF-MONITORING AND REGULATION OF BLOOD GLUCOSE

BACKGROUND

The present invention relates to a self monitoring device for attachment to the body, which incorporates real-time measurement of body movement and physiological analytes of metabolism (e.g. glucose) that can be modulated by physical activity. The device algorithm enables real time and personalised modulation of the selected physiological analyte(s) through cued activities and other evidence based clinical guidance dependent on previous and current analyte levels and previous and current patterns of movement.

The invention is particularly, but not solely, concerned with simple practical procedures that can readily be conducted by unskilled persons diagnosed with Type 2 Diabetes (T2DM) to provide reliable guidance on engagement in physical activity to regulate blood glucose levels and minimise the period of time spent in a hyperglycaemic state. The invention is also concerned with the independent and secure communication of body movement and physiological analyte levels together with evidence based clinical management information to skilled professionals within the person's clinical care team to assist in the management of the condition.

An important objective of the device is to enable persons with T2DM, supported by their clinical care team, to recognise the contribution that specific patterns of physical activity can have on glucose control and the reduction of time spent in hyperglycaemia and to guide sustained incorporation of these patterns of activity into everyday life to reduce long term risks of complications and cardiovascular disease arising from T2DM.

Many high quality studies have demonstrated the importance of sustained engagement in even low intensity physical activity to regulate physiological glucose levels and reduce the time spent in hyperglycaemia (e.g. "Continuous low- to moderate exercise training is as effective as moderate- to high-intensity exercise training at lowering HbA1c in obese T2DM patients" Hansen et al, Diabetologia 2009 52 1789-1797).

A recent position statement by American College of Sports Medicine and the American Diabetes Association (Med Sci Sports Exerc. 2010 December; 42(12):2282-303) summarises the current evidence bases and recommendations stating:

"Although physical activity (PA) is a key element in the prevention and management of type 2 diabetes mellitus (T2DM), many with this chronic disease do not become or remain regularly active. High-quality studies establishing the importance of exercise and fitness in diabetes were lacking until recently, but it is now well established that participation in regular PA improves blood glucose control and can prevent or delay T2DM, along with positively affecting lipids, blood pressure, cardiovascular events, mortality, and quality of life. Structured interventions combining PA and modest weight loss have been shown to lower T2DM risk by up to 58% in high-risk populations. Most benefits of PA on diabetes management are realized through acute and chronic improvements in insulin action, accomplished with both aerobic and resistance training".

The report discusses the benefits of physical training, along with recommendations for varying activities, PA-associated blood glucose management, diabetes prevention, gestational diabetes, and safe and effective practices for PA with diabetes-related complications.

Commercial technology for the continuous monitoring of blood glucose has been available for some ten years. The Abbott freestyle navigator is well validated and is employed by clinics for continuous blood glucose monitoring of patients with diabetes (http://www.freestylenavigator.com/index.htm).

A primary objective for such systems has been to improve glucose and insulin management in Type I diabetes (T1DM) (Reducing glycaemic variability in type 1 diabetes self-management with a continuous glucose monitoring system based on wired enzyme technology. Danne T et al. Diabetologia. 2009 August; 52(8):1496-503. Epub 2009 Jun. 13), development of closed loop insulin injection (artificial pancreas) systems (e.g. J Diabetes Sci Technol. 2009 Sep. 1; 3(5):1014-21, Closed-loop artificial pancreas using subcutaneous glucose sensing and insulin delivery and a model predictive control algorithm: preliminary studies in Padova and Montpellier. Bruttomesso D et al).

Avoidance of hypoglycaemia, especially nocturnally in T1DM, through the use of alarms associated with the measures glucose level has been a major objective (e.g. Diabetes Care. 2010 May; 33(5):1013-7. Epub 2010 Mar. 3. Prevention of nocturnal hypoglycemia using predictive alarm algorithms and insulin pump suspension. Buckingham B et al).

A recent review of clinical use of real-time continuous glucose monitoring (Curr Diabetes Rev. 2008 August; 4(3):218-22 by Battelino T & Bolinder J) reasonably summarises the current clinical perspective for the use of available technologies:

"Maintaining near-normal glycaemia in all patients with diabetes mellitus (DM) has become a standard and a well accepted recommendation. Unfortunately, most people with DM do not achieve this clinical goal because of marked glycaemic fluctuations and hypoglycaemia. Real-time continuous glucose monitoring (RT-CGM) has been introduced recently into clinical practice offering more knowledge about current glucose concentration and trend and enabling people with DM to intervene and prevent unwanted glucose excursions by acting upon real-time and predictive alarms. Several RT-CGM devices proved to be sufficiently accurate and feasible for routine use. Observational reports with The Guardian and Paradigm RT by Medtronic, the STS by DexCom, FreeStyle Navigator by Abbott and GlucoDay by Menarini established initial clinical benefit. Five randomised controlled trials (RCT) demonstrated significantly improved glucose variability or metabolic control, one of them showing a statistically significant and clinically meaningful decrease of HbA1c with a 3 months use of the Guardian RT (Medtronic, Northridge, Calif.)".

And concludes:

"The great potential of RT-CGM devices to improve daily glucose control and quality of life in people with DM can only be developed further through RCTs, clarifying in more details the optimal clinical use and the most beneficial indications for this novel technique".

Commercial technology for continuous monitoring of physical activity has been available for decades. The Sensewear system is a recently developed system reflecting the current state of the art and employs embedded MEMS accelerometers together with other sensors to measure body movement, temperature and skin conductivity on the upper arm to estimate measures of physical activity and energy expenditure (e.g. Br J Sports Med. 2010 July; 44(9):657-64. Epub 2008 Jul. 15. Validity of physical activity monitors in adults participating in free-living activities. Berntsen S et al) and such devices are increasingly employed in clinical studies requiring continuous monitoring of physical activity in free living persons (http://sensewear.bodymedia.com).

Pedometers and accelerometers have been widely used to promote increased engagement in physical activity for many decades and are increasingly integrated into web/mobile based systems to deliver lifestyle change programmes to improve health and wellbeing (e.g. J Med Internet Res. 2007 Apr. 27; 9(2):e7. Using internet and mobile phone technology to deliver an automated physical activity program: randomized controlled trial. Hurling R, Catt, M, Boni M D, Fairley B W, Hurst T, Murray P, Richardson A, Sodhi J S).

Accelerometer based devices have been employed in studies directed at improving glucose management in T2Dm. A recent pilot study (Diabetes Technol Ther. 2009 February; 11(2):113-8. The use of an Energy Monitor in the management of diabetes: a pilot study. Voon R, Celler B G, Lovell N H).

In this small study, five people with diabetes were given a triaxial accelerometer-based energy monitor that measured energy levels associated with activities of daily living. Participants wore the device for 3 months and continued their usual diabetes therapy. Glycosylated hemoglobin (HbA(1c)) was recorded to assess improvement in blood glucose control. The authors observed a a significant reduction of HbA(1c) from 7.48+/−1.21% to 6.98+/−1.44% (P<0.05) and that individuals engaged in physical activity at higher energy levels recorded much lower fluctuations in blood glucose level change between meals compared to those engaged in low physical activity levels. The study was also indicated promising results with respect to continued engagement with the weekly mean activity score showing an increase in activity levels from the second week to the final week.

The authors conclude:

"This pilot study demonstrated that the Energy Monitor could improve the management of diabetes by allowing people with diabetes to view and manage daily physical activity in addition to their usual diabetes therapy"

The combined use of continuous blood glucose and physical activity monitoring to motivate individuals with T2DM to engage in regular physical activity has been reported (J Clin Nurs. 2009 February; 18(3):373-83. Feasibility and acceptability of continuous glucose monitoring and accelerometer technology in exercising individuals with type 2 diabetes. Allen N A, Jacelon C S, Chipkin S R). The author's stated aim in this study was to develop role model data for a future intervention designed to motivate non-exercising individuals with type 2 diabetes mellitus to engage in regular physical activity. To explore this, the study described continuous glucose monitoring data and generated role model CGMS graphs and subsequently described a monitor to measure exercise amount and intensity to explore participants' experiences of the combined physical activity monitors and perceptions of the glucose monitoring data. The authors adopted a descriptive study design to describe physical activity patterns and glucose levels for 72 hours in nine exercising adults with type 2 diabetes. This was followed by a focus group interview to collect data from seven phase-1 participants. The authors analysed verbatim transcripts of the audio taped focus group for themes and trends. The authors describe how the glucose monitor data demonstrated lower glucose levels after exercise and how, compared to formal diabetes education, visual data from the glucose monitoring technology was perceived as more relevant to participants' particular, everyday experiences with respect to exercise, diet and stress. The authors state that participants reported a reinforced commitment to their exercise and diet regimens after using the continuous glucose monitoring system but also report technology issues such as discomfort when wearing activity monitors and issues relating calibration and event recording with the continuous glucose monitors.

The authors conclude: "Participants found that visual glucose monitoring data reinforced self-management behaviors, such as exercise. Our results suggest that data depicting the response of glucose levels to diet and exercise could be a useful tool to change behaviour in individuals with type 2 diabetes".

In a separate study (Diabetes Technol Ther. 2009 March; 11(3):151-8. Continuous glucose monitoring in non-insulin-using individuals with type 2 diabetes: acceptability, feasibility, and teaching opportunities. Allen N A, Fain J A, Braun B, Chipkin S R). continuous glucose monitoring is employed to provide contextual data lifestyle intervention for non-insulin-using, sedentary individuals with type 2 diabetes mellitus (T2DM). The study investigated CGM in terms of feasibility and acceptability and dietary- and exercise-teaching events. This study did not consider delivery of real time feedback and demanded careful, independent record keeping of individuals for subsequent review with their clinical care team. About half the participants (52%) reported difficulty remembering to enter events into CGM monitors, but most (82%) kept an accurate paper log of events. Users also reported difficulty maintaining reference blood glucose measures to maintain calibration of the CGM. The majority of participants were willing to wear CGM again despite reporting minor discomfort at sensor site and with wearing the monitor. CGM data provided several teaching opportunities in non-insulin-using adults with T2DM and despite the issues experienced, the authors found CGM to be acceptable and feasible.

There is evidence that light to moderate physical activity and reduced sedentary time can improve glucose disposal (e.g. Diabetes Care. 2007 June; 30(6):1384-9. Epub 2007 May 1, Objectively measured light-intensity physical activity is independently associated with 2-h plasma glucose. Healy G N et al). In this study of 67 men and 106 women (mean age+/−SD 53.3+/−11.9 years) without diagnosed diabetes, but with impaired glucose tolerance, physical activity was measured by particpants wearing Actigraph accelerometers during waking hours for 7 consecutive days. Activity data was summarized as sedentary time (accelerometer counts/min <100; average hours/day), light-intensity (counts/min 100-1951), and moderate- to vigorous-intensity (counts/min > or =1,952). An oral glucose tolerance test was used to ascertain 2-h plasma glucose and fasting plasma glucose. The authors found sedentary time was positively associated with 2-h plasma glucose (b=0.29, 95% CI 0.11-0.48, P=0.002); light-intensity activity time (b=−0.25, −0.45 to −0.06, P=0.012) and moderate- to vigorous-intensity activity time (b=−1.07, −1.77 to −0.37, P=0.003) were negatively associated after adjustment for confounding factors. Light-intensity activity remained significantly associated with 2-h plasma glucose following further adjustment for moderate- to vigorous-intensity activity (b=−0.22, −0.42 to −0.03, P=0.023).

Although existing management of T2DM blood glucose is predominantly focused on dietary management, the linkage between physical activity and blood glucose control is now well established. Reductions in sedentary time and light to moderate activities (e.g. walking) have been shown to associate with improved glucose control. Existing approaches to engendering increased physical activity in T2DM through communication of blood glucose control rely on analysis of past patterns of blood glucose and physical activity to educate the patient to promote a continued mindfulness to engage in increased physical activity. None of these have combined real-time monitoring of blood glucose (or other metabolites or analytes) levels with monitoring of movement or activity to correlate the two and to provide direct input to the patient as to how their activity can modulate their blood glucose levels.

SUMMARY

An object of the present invention is to provide real time instruction and feedback to the wearer based on current and previous glucose and activity levels to engender immediate action to better maintain glucose control and reduce time spent in hyperglycaemia. Such feedback not only reinforces the impact of immediate and recent behaviour on blood glucose control to improve mindfulness but provides an active means of modulating glucose levels by immediate prompted action.

A variety of technologies beyond basic movement detection by accelerometers attached to the body are now available to inform estimates of body movement, physical activity and energy expenditure such as GPS, heart rate monitoring, gyroscopes, wearable fabrics with dynamic properties in response to movement, optical measurement and cameras for example. Such technologies can enhance the assessment and classification of movement and activity but a simple device may be constructed using only an accelerometer attached to the body in association with appropriate technology to simultaneously monitor glucose.

The present invention relates to a system for the regulation of physiological analytes comprising;
    a movement sensor;
    a physiological analyte sensor;
    an output device for providing a signal to a subject; and
    a data processing module
    wherein the movement sensor is adapted to take and record continuous or regular movement readings to determine the movement of a subject; the physiological analyte sensor is adapted to take and record continuous or regular readings of levels of one or more physiological analytes present in said subject; the data processing module compares readings with recorded historical readings to determine how movement of a subject effects the rate of change of the one or more physiological analytes; and the output device is adapted to provide a signal to the subject if the levels of one or more of the physiological analytes fit a certain profile.

Preferably multiple signals or prompts are available for selection for provision to the user and the signal provided to the user is selected depending on the rate and/or direction of change of analyte levels.

Signals may take the form of prompts for specific activities e.g. a 10 minute run or a 5 minute walk.

Preferably multiple signals or prompts are available for selection for provision to the user and the signal provided to the user is selected depending on whether historical data shows that previous prompts of the same type have been complied with.

Advantageously the system continuously evaluates the current glucose level in relation to the ideal glucose level. The system may suggest or guide the individual to a self-identified target glucose level that accommodates the known rate of change expected from that individual in their current physiological condition for specific activities which are compatible with the individual capability and other relevant psychological and environmental factors that may promote or limit attainment. The core algorithm used by the system aims to adjust the frequency and content of prompts or signals to improve underlying glucose disposal capability and maximise the likelihood of compliance to immediate prompts for physical activity in response to elevating/elevated plasma glucose directed at minimising the periods spent in hyperglycemia.

Preferably the output device is adapted to provide a signal to the subject if the levels of one or more of the physiological analytes fall out with a pre-determined range.

Advantageously the continuous or semi-continuous real time monitoring of both movement and physiological analytes such as glucose, allows for specified outputs to be triggered which suggest cued activities. For example in the case of an individual with Type 2 diabetes, if low movement and high blood sugar levels are sensed in combination, the subject can be cued by a predetermined output to begin an activity such as walking and the effect of the activity can also be monitored in real time. As the system is able to record the correlated movement and analyte readings it is able to identify the rate and direction of change of analytes and cue an appropriate response from the subject. Notably, it is able to personalise the response required is it will be able to determine from historical data what type of activity will result in an appropriate change to the analyte readings.

The data-processing system is able to update in real time, which is understood to cover a system that can update and process information at the same rate as it receives data. Such a system is able to process information that it receives sufficiently rapidly to be able to control output responses.

The data processing module performs the function of determining whether the sensed levels of physiological analytes fall within a predetermined range. It can also then determine which output signal is most appropriate.

The data processing module can also calculate a measure of total movement or types of movement.

The data processing module can also calculate the rate of change of the selected physiological analyte levels and/or the direction of change of selected physiological analyte levels.

The ability to calculate the rate of change and direction of change of physiological analytes such a glucose allows the system to send an appropriate signal to the user in a timely manner. For example, where the system identifies a rapid increase in glucose levels the subject could be signalled to partake in moderate to vigorous exercise in order to avoid hyperglycaemia. For a less rapid increase in glucose the signal may only suggest low to moderate exercise. This guidance will be individually tailored relative to the historical data collected from the user. As change in glucose levels and movement, or more preferably an identified activity type, are correlated in real time (see FIG. 4) the system is able to effectively learn which activities result in which rates of glucose clearance and can tailor the prompts appropriately. This results in a system that is able to adapt to and with a user and which takes account of physiological & psychological elements that may effect the system such as;
    what level of physical activity can individuals engage in (physiologically and psychologically)?
    fitness/capability/disability
    physical activity efficiency
    muscle mass
    glucose disposal capacity: insulin sensitivity
    metabolic risk factors Diurnal rhythm, genetics, phenotypic factors
Type of physical activity
changing body mass, (other physical phenotype factors)
individual relationship of movement sensor signal characteristics to specific p.a. undertaken by individual
observed changes in glucose level also 'calibrate'
specific sensor characterisations/calibrations (batch to batch, site)

Optionally the system further comprises a data storage module which stores historical readings from the sensors.

The data storage module may be integrated into the processing module.

The data storage module may be remote from the subject.

Preferably the system comprises a clock.

Preferably the processing module is able to compare real-time readings with previous historical readings.

The data storage module allows historical data to be stored. The processing module can then compare current readings to historical data to allow personalisation of cued outputs. For example, historical data may indicate that only a low level of movement was previously associated with a reduction of blood glucose levels at a particular level—thus if this level is noted again a prompt to the subject to partake in low level activity could be sent. However if a spike in analyte levels is noted, the historical data may suggest more vigorous levels of activity are appropriate and this will be indicated to the subject by an appropriate output.

Optionally movement and analyte readings over a set time period can be analysed by the data processing module and target activity levels set for a forthcoming time period.

For example the number of times analyte levels have fallen out with a predetermined range in a 24 hour period can be determined e.g. where blood glucose levels have increased to hyperglycaemic levels, and a target activity level can be given for the next 24 hour period to improve the control of the analyte levels.

It may be desirable to use multiple movement sensors of the same or differing types. This could allow for differentiation between different types of activities.

Optionally the movement sensor comprises a pedometer.

Preferably the movement sensor records movement in at least one, preferably two and more preferably three axes, with a dynamic range of at least +/−2 g.

Preferably the movement sensor records movement with a dynamic range of at least +/−2 g.

Preferably the movement sensor records movement with a dynamic range of at +/−8 g.

Preferably the movement sensor comprises an accelerometer.

The accelerometer may be single of multi-axis.

Advantageously, the accelerometer is able to measure acceleration at the point of contact with the body.

Preferably the accelerometer is configured to acquire acceleration estimates on each axis at a sampling frequency of at least 10 Hz.

Preferably the accelerometer is configured to acquire acceleration estimates on each axis at a sampling frequency of at least 8 Hz, and more preferably at least 10 Hz.

Most preferably the movement sensor comprises a triaxial accelerometer.

Optionally the movement sensor comprises an gyroscope.

A gyroscope provides angular and absolute positioning and orientation as well as trajectory data.

Optionally the movement sensor is a MEMS based accelerometer.

Optionally the system may further comprise temperature sensors and/or skin conductivity sensors.

Preferably the movement sensor is provided with means for associating said sensor with the body of a subject.

Preferably the physiological analyte sensor senses glucose levels in a subject.

Most preferably the physiological analyte sensor is a continuous glucose measurement sensor.

Alternatively it is a frequently sampling glucose monitor where the sample frequency is >5 minutes, more preferably >1 minute, more preferably >30 seconds.

Preferably the physiological analyte sensor is non-invasive or minimally invasive.

Optionally the physiological analyte sensor is a microneedle array based sensor.

The physiological analyte sensor may be an optical sensor. This may utilise raman spectroscopy, M/R spectroscopy or N/R spectroscopy. Alternatively it may utilise kromoscopy, photo-acoustic spectroscopy, optical coherence tomography, scattering/occlusion spectroscopy, polarimetry, thermal infrared or fluorescence.

Alternatively the physiological analyte sensor is transdermal. Preferably this may utilise impedance spectroscopy or reverse iontophoresis. It may also utilise skin suction blister technique or sonophoresis.

The physiological analyte sensor could also be an invasive sensor such as an intravenous implantable sensor, a microdialysis device or an invasive subcutaneous sensor although this is not preferred.

Optionally the output device comprises one or more of a visual, audible or tactile output.

Preferably the output device comprises a viewing screen.

Preferably the output device comprises means for providing real time location information.

Optionally the means for providing real time location information is a global positioning system receiver.

Providing location information which can be linked to movement and glucose readings in real time allows for further identification of the types of activity being carried out. It also allows the system to identify human proposlion compared to mechanical propulsion for example.

The invention also relates to a method for the regulation of physiological analytes which utilises the system described above wherein a movement sensor takes and records continuous or regular movement readings to determine the movement of a subject; levels of one or more physiological analytes present in said subject are taken and recorded; readings are compared to recorded historical readings to determine the rate and direction of change of the levels of one or more physiological analytes and the associated levels of physical activity; and if the levels of one or more of the physiological analytes fit a certain profile a signal is sent to the subject.

Preferably there are multiple signals are available for selection for provision to the user and the signal provided to the user is selected depending on the rate and/or direction of change of analyte levels.

Preferably multiple signals are available for selection for provision to the user and the signal provided to the user is selected to prompt a known activity which, in accordance with historical data, will direct analyte levels in a desired direction.

A recent review summarises current and emerging technology for in-vivo glucose sensing (Diabet Med. 2009 March; 26(3):197-210. Glucose sensors: a review of current and emerging technology. Oliver N S, Toumazou C, Cass A E, Johnston D G.) The authors summarise technologies and applications discussing traditional, enzymic optical and electrochemical sensors typically used to assess glucose via r periodic finger prick (or forearm) blood samples, the emergence of continuous blood glucose sensors in the past decade demanding sub-cutaneous placement of the sensor through to trans-cutaneous microneedle interstitial fluid extraction, reverse iontophoresis and non-invasive optical and thermal methods. These authors also envisage such continuous sensors as facilitating the realisation of closed loop insulin delivery but do not discuss the utility for real time lifestyle modification of diet and physical activity.

The current UK guidelines (NICE 2008) for Type 2 diabetes (National Institute for Health and Clinical Excellence (NICE) (2008) Type 2 diabetes: the management of Type 2 diabetes. Clinical guideline 66. NICE: London) recommend the maintenance of blood glucose levels before meals in the range 4-7 mmol/l and at two hours after meals to maintain blood glucose below 8.5 mmol/l. The management approaches identified are entirely dietary based with physical activity recommendations as part of the overall lifestyle recommendation rather than as an active modulator of immediate blood glucose levels.

The current invention is conceived as a means of integrating physical activity into real time blood glucose control. It may be used to educate and promote behaviour change, providing individuals with T2DM with immediate prompting for engagement in physical activity and feedback on the impact of that physical activity on glucose control and the time spent in hyperglycaemia. This approach reinforces the benefit and impact of even low to moderate physical activity, ensures real time assimilation of the contexts where physical activity can contribute to glucose control and facilitate the recognition and adoption of improved glucose management behaviours. The system may be used continuously or part of a specific and finite duration T2DM lifestyle management course. The invention is not intended to substitute for strict blood glucose management methods required for insulin dependent diabetes.

BRIEF DESCRIPTION OF THE DRAWINGS

In order to provide a better understanding of the present invention various example will now be described with reference to the following figures in which.

DETAILED DESCRIPTION OF ILLUSTRATIVE EMBODIMENTS

Figure 1:
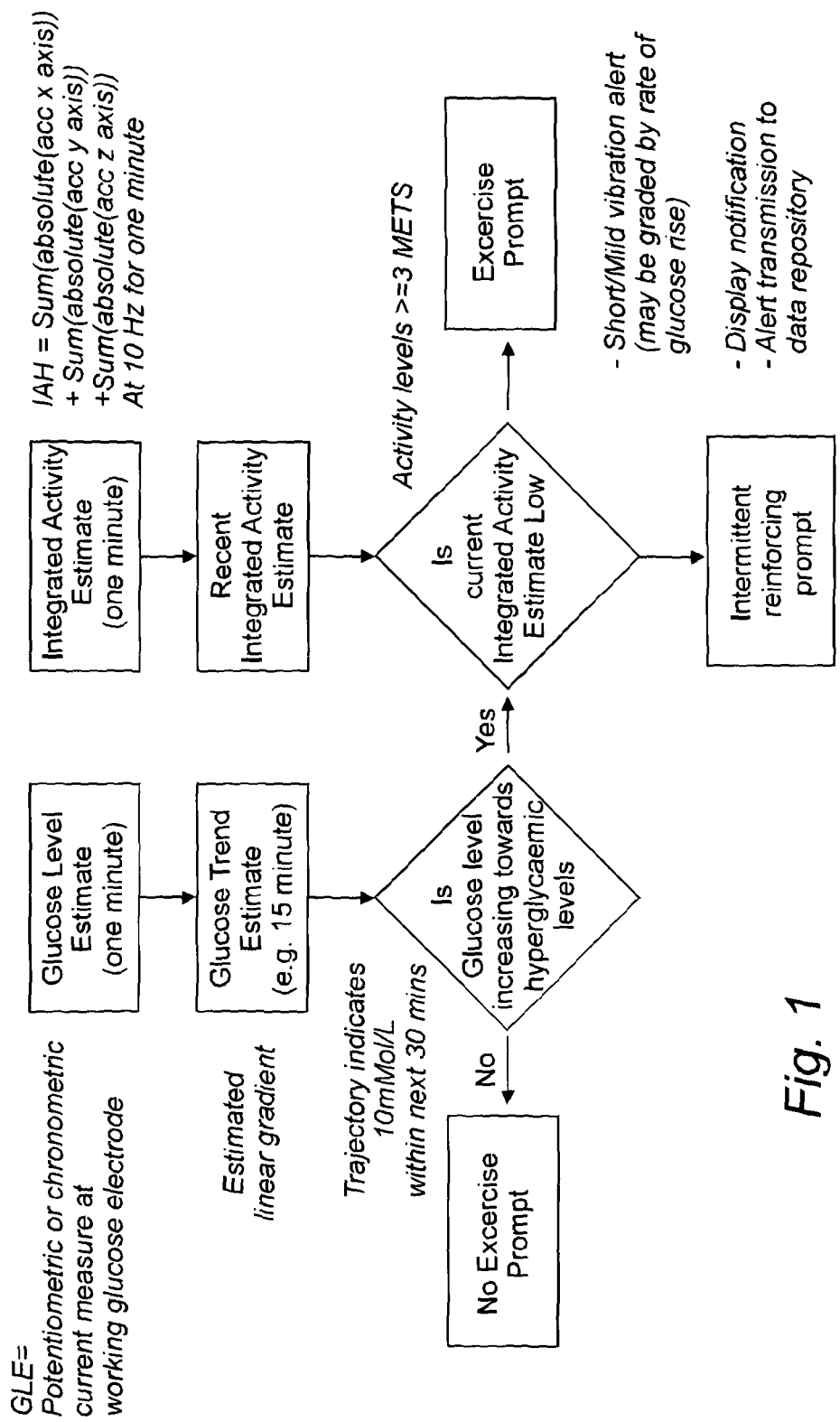
FIG. 1 shows an example scheme for real time exercise prompting from combined continuous glucose and movement measures.

It will be appreciated that the embodiments described describe elements such as the various options for sensor which may be interchangeable and that individuals or devices may be equipped with single or multiple sensors of the same or different types. For example a simple embodiment may employ only a single movement sensor e.g. a tri-axial accelerometer and a continuous glucose monitor.

In one embodiment, there is provided a device incorporating a micro-needle construct as a continuous glucose monitor as this technology has now been under development for continuous glucose measurement for over a decade and access to this technology has been established for demonstration of the invention. The invention may also be realised via other glucose sensing modalities, especially reverse iontophoresis and other non-invasive approaches (e.g. optical measurement using raman spectroscopy). The ideal embodiment must present a low barrier to continuous wear/usage and adequately reflect glucose status for a lifestyle intervention. The technology need not fully meet the requirements for traditional glucose monitoring as the invention can be used in addition to rather than as a substitute for accepted blood glucose measurement technologies in diabetes management. The technology should be affordable for general use and be minimally invasive to every day activity for free living individuals. Consideration must be given to comfort, reliability, reproducibility and the potential to provide actionable instruction and feedback.

The Abbott freestyle navigator to collect continuous blood glucose estimates at one minute intervals with concurrent monitoring of physical activity using the sensewear device to collect estimates of physical activity (energy expenditure & step counts) to develop some aspects of the underlying algorithms for the integrated continuous blood glucose and movement measurement system described here. The glucose monitoring device comprises a disposable sensor element which can be inserted under the skin (for up to 5 days) and which is able to take interstitial plasma readings to provide a user with glucose measurements every minute. The readings are displayed in real time on a wireless receiver.

Example I: comprises an armband incorporating a MEMS based accelerometer designed to accommodate and connect to a micropore or microneedle array based glucose sensor affixed to the upper arm of the wearer. An example of a suitable MEMS based accelerometer is the ST Microelectronics LIS331DLH (http://www.st.com) digital accelerometer designed to interface simply to a microcontroller. Other MEMS devices are available and suitable for this applications and should preferably achieve a similar or smaller package size, similar or lower current consumption for acceptable battery lifetime and similar or better measurement performance of the device indicated. The selected device should record human movement in at least one, preferably two and more preferably three axes with a dynamic range of at least +/−2 g and more preferably +/−8 g or higher and preferably deliver good sensitivity per bit (e.g. 4 mg/bit or better) to assist in detection of non-wear, physical inactivity classification, physical activity classification and other ancillary features. The device should be configured to acquire acceleration estimates on each axis at a sampling frequency of at least 10 Hz and preferably not less than 8 Hz. A yet simpler device might simply employ recognised principles of pedometer design to detect steps.

The microneedle glucose sensor array employs conventional enzyme based electrochemical measurement technology that can yield electrical signals indicative of glucose level in the recovered biological fluid when measured with a conventional potentiostat circuit optimised to the electrode, enzyme and sample properties.

Examples of microneedle blood extraction and glucose measurement devices are described in the scientific literature (eg. Biomed Microdevices. 2005 December; 7(4):347-53. Development of blood extraction system for health monitoring system. Tsuchiya K, Nakanishi N, Uetsuji Y, Nakamachi E).

In the example device, an array of dermis penetrating, hollow microneedles draw interstitial fluid by capillary action into an integral analytical chamber containing immobilised reagents for glucose determination connected by a short diffusion path for small molecules such as glucose. A connector is provided to the armband assembly to provide electrical connection to the electrode constructs and provide secure support for the sensor. In the preferred approach, microneedle arrays are applied to the skin after skin surface preparation firstly by mild cleaning to ensure cleanliness and secondly with mild abrasion to reduce epidermal thickness and ensure secure and reliable sample recovery The potentiostat circuitry may be interfaced to a real-time microcontroller via conventional analogue to digital conversion technologies. A classic example of a compensating microelectrode amplifier is described in Horowitz & Hill, "The art of electronics", ISBN 0 521 37095 7 (p 1014) An example microcontroller for this application may be selected from the PIC 24 family (http://www.microchip.com/). An example device with integral usb for easy interfacing and data recovery to another computer, integral A/D for the potentiostat and i2c communication for the accelerometer is the PIC24FJ64GB106 but other devices may be selected from microparts or other manufacturers supplying comparable products.

Power for these components can be supplied by a compact Li-polymer battery. Many suppliers exist for these batteries. An example supplier is YunTong battery (e.g. http://www.yuntongbatt.com/v2007/products.php?fid=5&tid=138&typename=0-500mAh+&zid=37) and given reasonable consideration to power requirements & comfortable packaging dimensions and light weight for a device of this kind, the YT482030 230 mAh, (4.8×20×30 mm, 5 g weight) battery provides acceptable reserve for several days operation of the glucose sensor, accelerometer, microcontroller, display and associated circuitry to make a functional device.

User interaction to start and configure the device may be accomplished through generic techniques (e.g. actuator switches) and communication of instructions and feedback to the wearer via conventional display technology. In the preferred embodiment, the instructional and advice display is separated from the armband and embodied in a separate unit to allow easy access and viewing when the armband may be concealed by clothing but discrete interaction with the wearer can be achieved using readily available vibrating alarms such as used in mobile phones (see for example the system setup of FIG. 3).

External communication may be established by commercial wireless technology or via fast serial communication (e.g. usb). A variety of wireless systems our available. An example is provided by Bluetooth technology (http://www.bluetooth.com) which has the advantage of enabling direct communication of data via mobile phone and other readily available IT devices. development packages for the development of software applications on mobile phones are widely available from the major manufacturers and mobile systems providers (e.g. Apple, Google Android etc). The invention is compatible with other means of user interaction such as vibration alerts and sound.

Inclusion of a mobile phone in the system may provide not only immediate feedback to the wearer but also transfer data with a central data repository accessible by web and mobile technologies for later inspection and interpretation.

Figure 3:
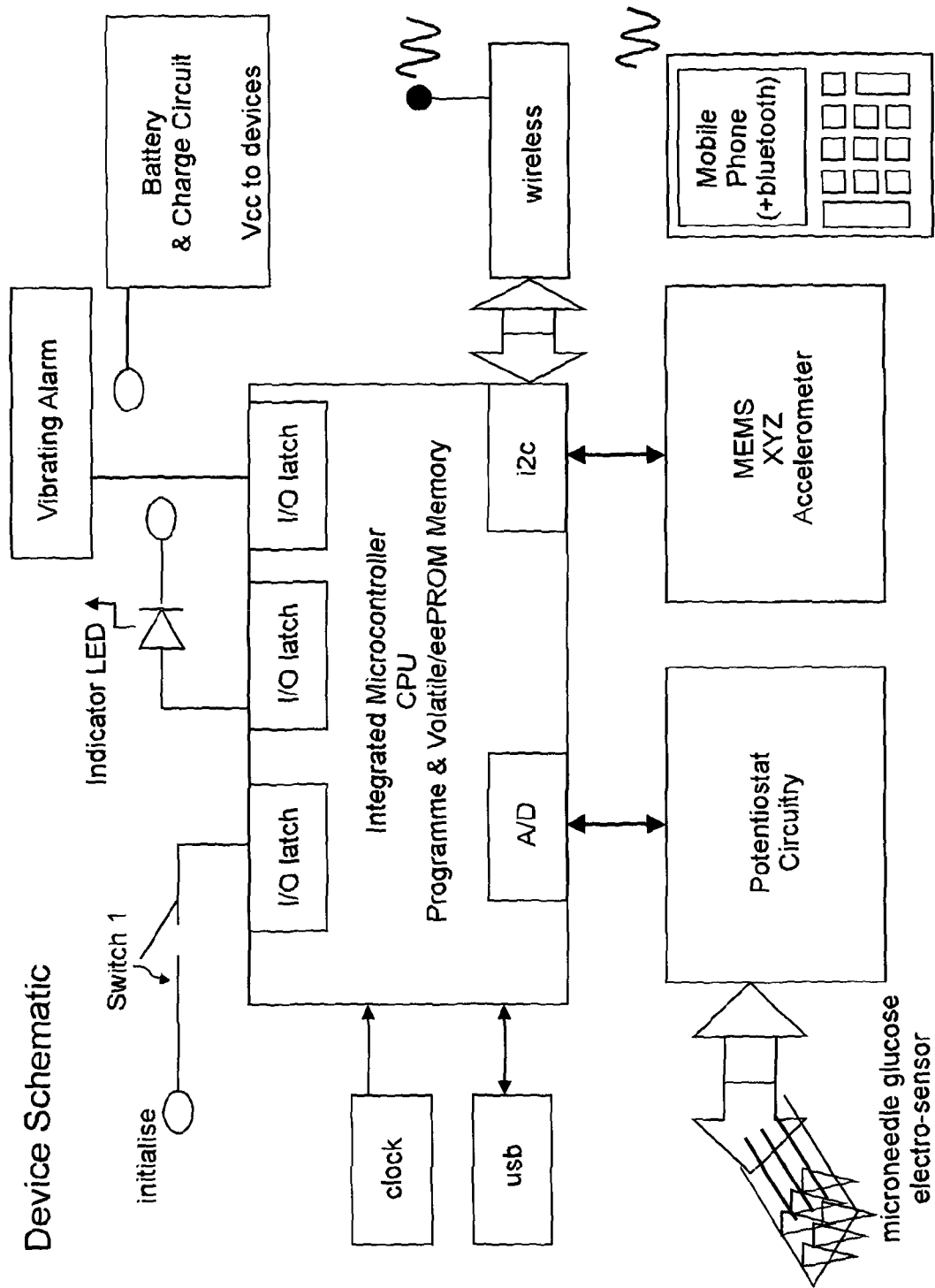
FIG. 3 is a schematic showing a typical device that could be used in accordance with the present invention.

The device may operate independently of the mobile phone communicating to the wearer through user an integral user interface as illustrated in FIG. 3.

Commercial product design techniques allow the essential components and the connection to the microprobe glucose electrosensor to be appropriately packaged for comfortable and continuous wear on the upper arm. A light elasticated cuff with Velcro™ adjustment is appropriate for such a design. An alternative design might locate the glucose sensor at an alternate site (e.g. abdomen) and packaging would be modified appropriately.

With the device programmed appropriately and with sufficient charge in the battery, the wearer may affix the microprobe glucose sensor to the upper arm as described and connect to the integrated armband controller incorporating the accelerometer. Actuating the initialisation switch enables the device to perform internal self test routines, link to and test the microprobe sensor for stable function as well as initiating connections to any external paired mobile device for remote data communication.

Figure 4:
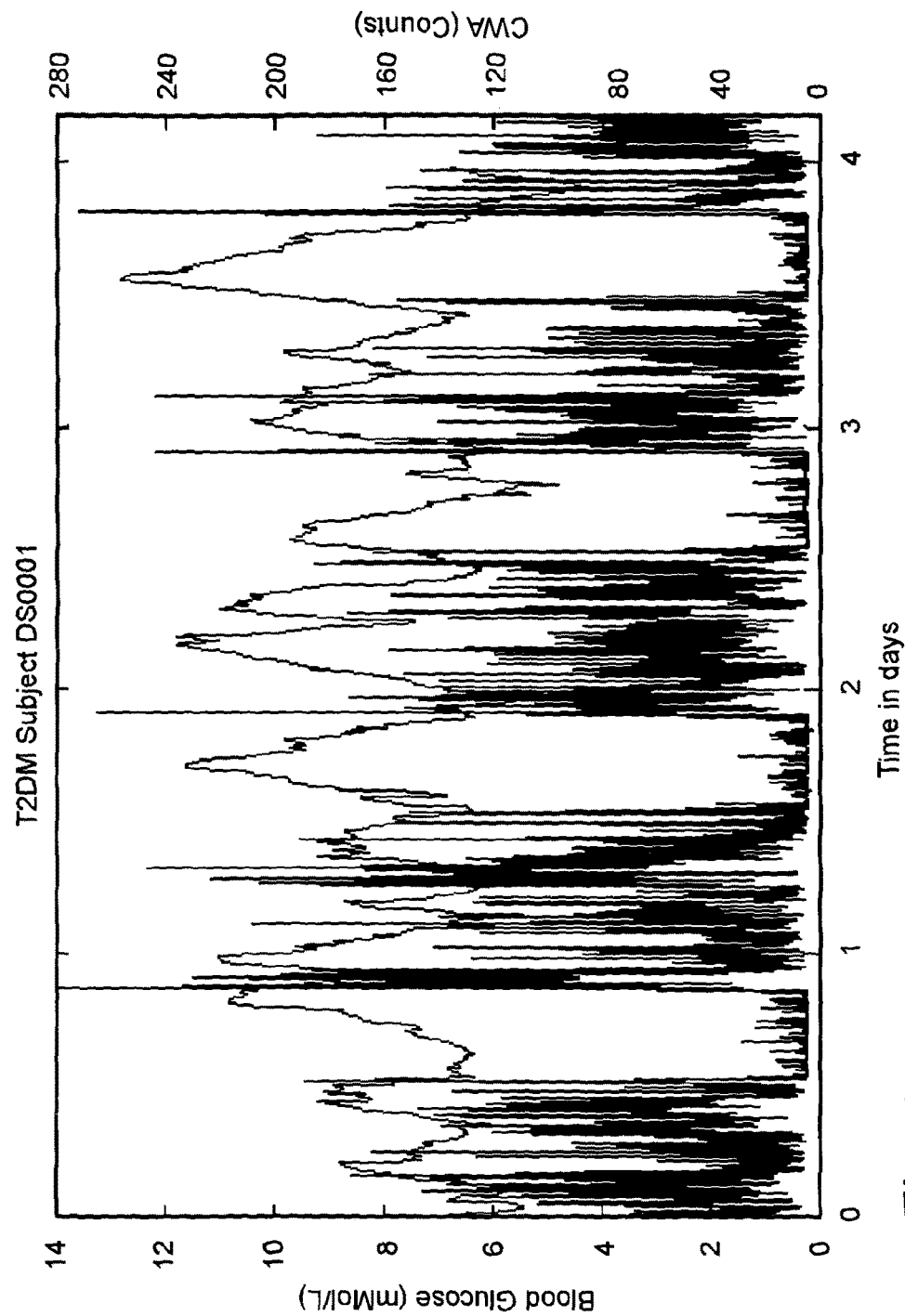
FIG. 4 is a graph showing the combined results of continuous glucose monitoring and movement in a subject.

During normal operation the glucose level will be measured at frequent intervals through the day. The measurement may be continuous or regular, although continuous is preferred. When considering regular readings, an interval not exceeding five minutes is preferred for this application. A one minute interval or less is more preferred. This also covers the option of the glucose monitor effectively monitoring glucose levels continuously but only taking an recording a reading at intervals. The accelerometer samples acceleration on each axis at the selected frequency continuously during normal wear. An example readout is shown in FIG. 4 where the correlated glucose levels and activity levels can be seen. A variety of alternative approaches have been described for the processing of accelerometer data to provide indices of movement. An example of the calibration of a triaxial accelerometer device output to give reliable and valid estimates of human energy expenditure is described in (Med Sci Sports Exerc. 2010 Nov. 11. Validation of the GENEA Accelerometer. Esliger D W, Rowlands A V, Hurst T L, Catt M, Murray P, Eston R G) with observed criterion validity against a reference energy expenditure measurement (VO2). More sophisticated methods can classify activity types and thus provide detailed feedback and instruction to the wearer (e.g. J Appl Physiol. 2009 September; 107(3): 655-61. Epub 2009 Jun. 25. Improving assessment of daily energy expenditure by identifying types of physical activity with a single accelerometer. Bonomi A G, Plasqui G, Goris A H, Westerterp K R).

For a simple illustration of the invention, the data processing may be confined to a measure of step counting or integrated activity measurement. A simple and appropriate method of operation using an integrated measure of total movement to illustrate the invention is to sum the absolute acceleration values on each axis between glucose measurements and then sum these individual axis quantities across all axes to yield a total measure of new movement since the previous glucose measurement. These measures may be stored within the device or transmitted wirelessly for later inspection and interpretation and for use in personalising the output to the user.

The electrochemical measure indicative of glucose at the site of measure must be separately calibrated to relate to established measures of blood glucose to establish normal, hypo- or hyper-glycaemia. Discussion of the relationship between different measures of blood glucose are described in (Ann Clin Biochem. 2008 March; 45(Pt 2):140-8. Measurement of blood glucose: comparison between different types of specimens. Carstensen B, Lindström J, Sundvall J, Borch-Johnsen K, Tuomilehto J; DPS Study Group). For any individual wearer, periodic blood glucose measurements can be made using an approved glucometer to relate signals recovered from the microneedle electrosensor to reference measures. Continuous glucose sensors may exhibit some change in response over time such that the calibration should be checked at intervals appropriate for the sensor characteristics. Acceptance criteria for the operation of the sensor can be derived from the stability and drift (as reflected in the relationship to periodic reference method measures) and the need for sensor replacement indicated to the wearer via the associated display. Existing technology permits the automatic linking of reference blood glucose measures to the microneedle electrosensor although this linkage can of course be maintained by direct input of the reference values via the user interface also.

FIG. 1 illustrates a scheme for immediate guidance to the wearer which can be generated by consideration of the trend in recent measures of glucose and estimates of recent physical activity. An upward trend in glucose measurements over the previous fifteen minutes against a low level of physical activity can be used as a prompt to directly communicate the benefit of immediately engaging in physical activity, even at a low to moderate intensity such as achieved by walking. The prompt to engage in physical activity may be by direct communication through the vibrating alarm, a discrete sound cue or via a message generated on the associated display either integrated into the device (e.g. LED) or a message display on the paired mobile phone.

The generation of the alert can be recorded within the device or transmitted to the data repository for later inspection and interpretation by the patient clinical care team.

Ten minutes walking at 3 mph for an 82 kg person will consume around 40 Calories of energy. Each gram of carbohydrate is capable of yielding 4.5 Calories. This is the equivalent of c.a. 900 mg/min glucose burn. A recent estimate (The Journal of Clinical Endocrinology & Metabolism Vol. 94, No. 9 3530-3534, Estimated Glucose Disposal Rate in Assessment of the Metabolic Syndrome and Microvascular Complications in Patients with Type 1 Diabetes. Chillarón et al) of glucose disposal rates in normal non-diabetic individuals of 9.93±1.6 mg/kg-1·min-1 would equate to 740 mg/min in an individual weighing 82 kg. Individuals with metabolic syndrome in the same study show glucose clearance rates of 6.19±1.5 mg/kg-1·min-1. Studies have shown glucose clearance rates to increase in non-diabetic controls during exercise. For example, supine cycling in normal healthy mails increased glucose disposal rate by 70%, limited by glucose availability (J Appl Physiol. 1990 November; 69(5):1689-94. Effect of exercise on glucose disposal: response to a maximal insulin stimulus. Bourey R E, Coggan A R, Kohrt W M, Kirwan J P, King D S, Holloszy J O). In a study comparing whole body glucose disposal rates in T2DM subjects before and after a three month exercise intervention (Diabetes Obes Metab. 2008 May; 10(5):400-7. Non-oxidative glucose disposal is reduced in type 2 diabetes, but can be restored by aerobic exercise. Yokoyama et al) the GDR improved (2.93+/−1.55 mg kg-1 min-1 vs. 4.55+/−1.83 mg kg-1 min-1, p=0.001).

A daily physical activity level integrating the equivalent of 40 minutes of walking daily has been shown to deliver significant impact on glucose control and reduce the long term costs of care associated with T2DM management. This establishes a target activity level that can be titrated in 10 minute walking/physical activity episodes to increase or decrease individual daily activity levels relative to this level and according to the level of success the individual achieves in maintaining good glucose control evidenced by time spent in hyperglycaemia episodes. Individual metabolic status and compliance with standard recommendations on dietary control would lead to adjusted physical activity recommendations for each individual. The advantage of the present invention is that the impact of episodes of physical activity can be related to glucose control both immediately and in the context of the current day. Real time prompting can engender engagement in physical activity around meal times. Improvements in glucose management arising from improved whole body glucose disposal derived from increased exercise can be directly communicated to the wearer to promote sustained adoption of healthy physical activity levels.

Figure 2:
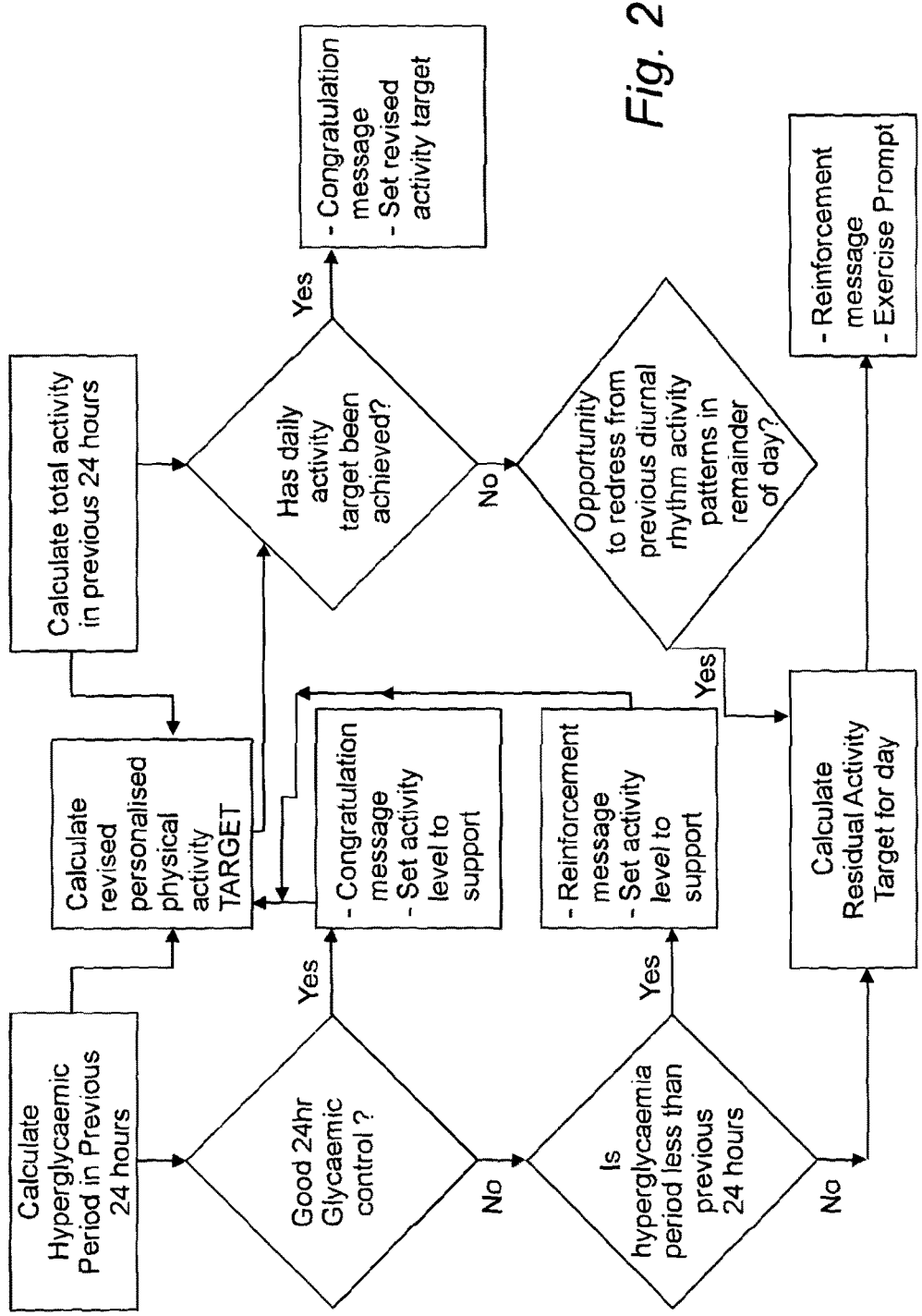
FIG. 2 shows a general scheme for daily glucose and physical management.

A general scheme for daily glucose and physical management is shown in FIG. 2:

This scheme illustrates how continuous glucose measurement can influence immediate recommendations for physical activity during the day over and above immediate prompting based on short term trends in glucose. Taking into account the known benefits from achieving a 40 minute daily walk, a personal target can be set based on the realisation of daily glucose control targets. Further benefit can be derived from consideration of dietary factors. For example, an individual achieving high activity levels but still exhibiting periods in hyperglycaemia can receive additional dietary advice X. The specific meal occasions contributing (breakfast, mid day, evening or snacking) will be evident within the glucose profiles. An individual struggling to meet a personal daily activity target can receive additional prompts at appropriate sedentary periods during the day to engage in increased physical activity (e.g. 10 minute walk). Individuals can also be engaged in setting their own physical activity goals to improve glucose management (e.g. based on evidence based recommended targets for the individual).

Calibration

The system may also wish to provide real feedback on how periods of physical inactivity, physical activity and sleep influence metabolism and circulatory glucose levels at any single point in time. This feedback will be tailored to an individual, learning over time how patterns of physical inactivity, physical activity and sleep influence circulatory glucose levels.

To accommodate the factors affecting circulatory glucose level and glucose disposal, the system must optimise the use of the physical activity sensing to ascertain the impact on glucose disposal and time spent in hyperglycaemia by consideration of other contextual and physical factors controlling this relationship.

The system will undergo a period of wear for calibration where it will tailor individual feedback on metabolism and glucose disposal based upon; movement (physical inactivity, physical activity, exercise), sleep, and information on diurnal glucose levels.

Calibration methods depend on the number of devices/axes and sites of attachment and either the relationship between an index of integrated movement and energy expenditure or, more recently, with some contextual information to improve the estimate of energy expenditure (i.e. activity classification). For example accelerometers on the hip are notoriously limited in being able to estimate energy expenditure from cycling. When attached to the wrist or hip accuracy in determining movement patterns is improved. Specific features can be identified in the signal that help to classify the activity as cycling but energy expenditure level is difficult to estimate as the movement index or features may not adequately relate to the degree of exertion.

In the present case we will associate not only with energy expenditure, but with glucose disposal rates with a focus on (A) low-level 'basal' physical inactivity and physical activity patterns and (B) periods of more vigorous physical activity and exercise.

The availability of specific contextual information on the nature and intensity/duration of the physical activity, the muscles employed and the metabolic, fitness, genetic/phenotypic characteristics of the individual will greatly affect the relationship between physical movement (or lack of) and circulatory glucose clearance. A sophisticated algorithm can be described that integrates the impact of these factors both on first usage (initial genotypic/phenotypic characteristics of the individual metabolically and physically) but also continuously adapts to changing metabolism, physical characteristics (e.g. weight, muscle mass) and learning of relevant contextual information (e.g. by self annotation of activities). For example, the algorithm may consider that Age, high BMI, Period with T2DM may imply lower glucose disposal rate. Fasting glucose level can be predicted or estimated within first few days of wearing and individual characteristics of responsiveness to recorded levels of activity and their duration. Actual body mass and frame size will impact directly affect 'work done' on movement and indirectlty affect the way in which particular levels of activity are recorded. Physical Function (disability for example) may shape prescribed physical activity.

The movement sensor can be sensitive to intensity and duration of periods of activity and when these are conducted during the day (a) generally at population level (b) by this individual historically (c) changing physical activity patterns in the individual.

Using models of energy metabolism combined with observing direct effects of physical activity on glucose level can contribute to calculating amount of activity required for subsequent glucose level changes according to relative rate of elevation, absolute level.

Immediate Gains Might be Obtained in Encouraging Healthy Activity Patterns (Breaking Up Sedentary Behaviour)

An advanced algorithm can accommodate the diurnal changes in metabolic responsiveness to physical activity on glucose metabolism. Undisturbed sleep will lead to improved glucose disposal. Changing patterns of activity through the sleeping period can be used to infer sleep derived changes in glucose—insulin axis. Slow wave sleep influences glucose disposal. Movement monitoring is routinely used to accsses sleep quality. http://www.ccjm.org/content/78/8/549.full. For example as individuals age, it can become more difficult to transition to slow wave sleep. This manifests itself by waking early in the morning and accompanying activity as a result (often quite low intensity, but elevated above sleeping levels). Self annotation can also help to identify such characteristics. In elderly individuals, the diurnal rhythm may become affected by other chronic disease. This can be recognised by reduced differential between night and daytime activity levels, even to the extent of no clear nocturnal/day activity patterns.

Changing shift work is known to affect glucose metabolism adversely. Shifting activity patterns can identify this and send appropriate prompts to minimise hyperglycaemia accordingly. The correlation between activity and glucose levels allow the system to adapt the prescribed physical act.

In our case, we not only have the activity classification data, but also the continuous glucose data. The trajectory of the glucose can provide additional insight into intensity of the activity (e.g. cycling at different intensities will directly impact clearance rates). Fuel switching must be taken into account however with such interpretations.

Knowledge of the genotype and phenotype of the individual, including their historical levels of physical activity and previous metabolic profile can greatly assist in understanding the relationship between the movement sensor signals, glucose level and glucose clearance as well as the relationship with consequent time spent in hyperglycaemia.

Figure 5:
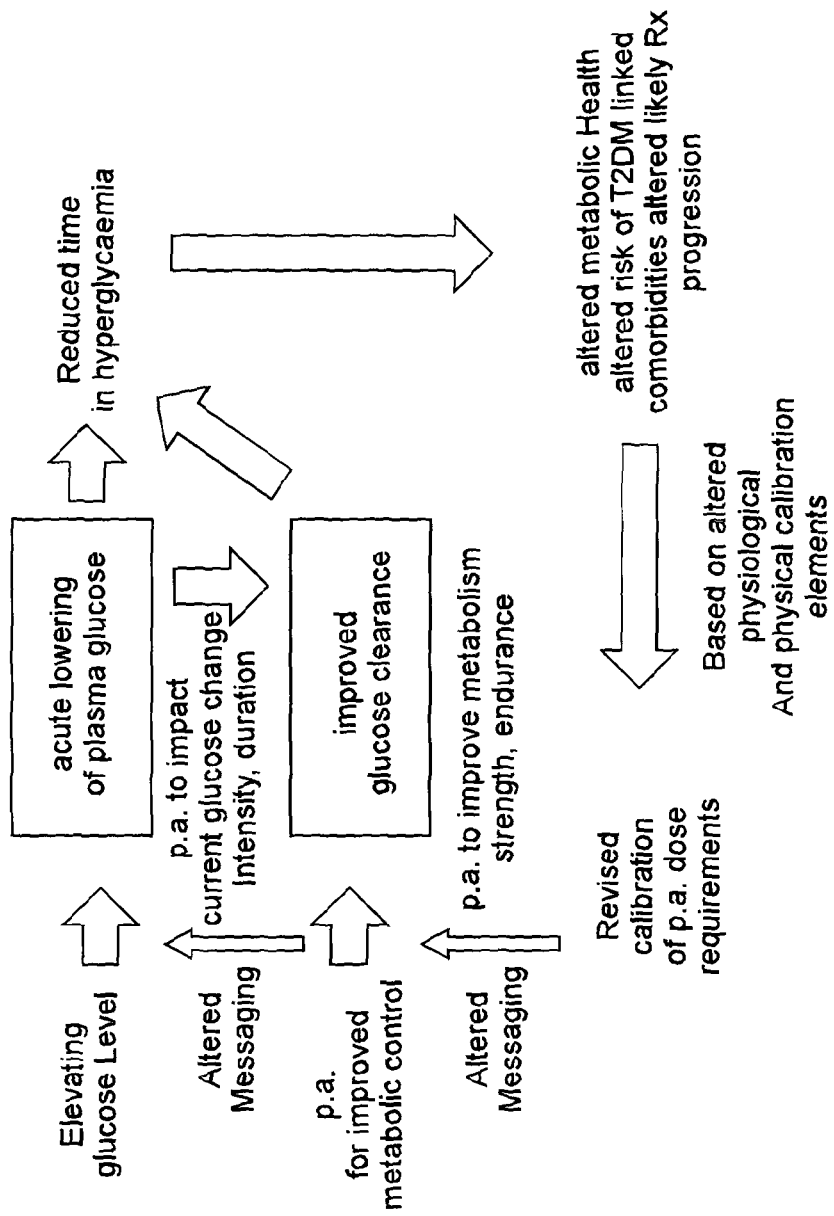
FIG. 5 shows a schematic for dynamic physiological calibration which allows personalisation of signal output to the users physical activity dose requirements.

Improvements in metabolic efficiency brought about by increased levels of physical activity will improve glucose clearance and reduce the period of time spent in hyperglycaemia for an individual with type 2 diabetes. Thus, as metabolic efficiency improves as a result of prolonged increased in physical activity (days and weeks) there will be a direct impact even on both basal glucose clearance and on acute clearance in response to physical activity as blood perfusion to muscle improves. FIG. 5 shows how the present system is able to revise outputs depending on the changing requirements of the user. This can utilise comparison of current reading to historical readings to determine changes in rate of glucose clearance.

It is a particular benefit of the present invention that the system can adapt with the user to provide personalised responsiveness. As the system records historical data it can compare glucose clearance rates for a particular activity level to historical glucose clearance rates at the same activity level to determine whether the metabolic efficiency of the user has changed. Prompts or signal to the user can then be adapted accordingly.

Feedback

Combined measurement of physical activity and circulating glucose levels can be used to provide guidance to the individual to minimise the period of time spent in hyperglycaemia as follows:

General

Instantaneous Feedback on glucose levels and their dynamic movement (moving higher, moving lover, or stationary). This can be at regular intervals, preferably of less than one minute, or can be real time recordal of data such that the information is processed and feedback to the user is sent at the time that the readings are taken.

Information about accumulated physical activity for that day.

Information about physical inactivity for a day.

Real time prompts about periods of physical inactivity.

Tailored

More specific tailored feedback will be provided following the calibration period giving individual information on current estimates of glucose clearance, metabolic efficiency, time of day, and individual context (especially if combined with social media, geotagging, self-tagging) data.

Prompting

FIG. 5 provides an overview of the prompting that can be triggered and also indicates how the system will provide a personalised response by regularly revising the calibration, or the predetermined ranges for prompts.

General Patterns:

Feedback can be provided on basal patterns of physical inactivity and physical activity to reduce patterns of physical activity that reduce glucose clearance and metabolic efficiency (generally periods of physical inactivity). It is also known that breaking up sedentary periods improves overall glucose/insulin control. The system can therefore also prompt physical activity to maintain a healthy balance of activity without extended sedentary/rest periods. If sustained, these periods of activity could result in improved glucose control, and as a result, the necessity for tailored feedback.

Acute Response:

More acute feedback can be used to prompt an acute period of increased physical activity or exercise in response to a rise in circulatory glucose levels. This period of physical activity or exercise is used to reduce hyperglycaemia. Prompting of physical activity can therefore be immediate in response to glucose level change and titrated according to genotype/phenotype/immediate context to minimise hyperglycaemic period. If sustained, these periods of activity and/or exercise could result in improved glucose control, and as a result, the necessity for tailored feedback. These bouts of activity might be specifically structured to incorporate mixed resistance and aerobic activity to improve glucose disposal. As the system is able to compare current and historical correlated glucose and movement data it can update as a users metabolism changes such that the appropriate prompts regarding types and levels of activity are sent.

Some degree of wearer control is required to ensure that advice is appropriate to the user context. This is likely to be derived from self-annotation and specific selection of system behaviour types (e.g.: suppression of advice for a period under wearer control).

Sleep hygiene: The system could be adapted to monitor periods of sleep, targeting 7-9 hours of sleep per night and with regular sleep-wake (diurnal) patterns and accommodate this behaviour within the calibration.

Peer Support Feedback

It is known that significant others (friends, partner, family) can influence physical activity behaviour. Linking the behaviour of the device to identified others (e.g. availability of a partner to engage in a walk for example from diary or social media link) can facilitate adoption of improved physical activity behaviour. Such media can assist in the planning and scheduling of joint activities that help to sustain a healthy active lifestyle. These community based activities can help support levels of basal physical activity as a means to improve glucose disposal.

Feedback will be provided to identified others as permitted by the user on general patterns of activity, glycaemia and through email, text, social media and the internet. This information will be used to reinforce positive behaviour change. The identified others will also be able to provide feedback and support through these media.

Lifestyle intervention involving peer group linkage has also been shown to be effective in promoting healthy behaviour change. The engagement of family and friends in support of individuals in T2DM has also been shown to contribute to improved glucose management. The advent of social networking now presents increased opportunity to engage family, friends and other peer groups in support of individuals with T2DM or other chronic diseases that respond to lifestyle intervention. The present invention accommodates the provision of additional information, advice and instruction to selected members of the patients family, friends and other peer groups following appropriate approval by the patient, the managing care team and the individuals concerned. The system will provide for appropriate data control and privacy measures'.

A specific example is to encourage a close family member to engage in additional physical activity, such as walking, with the individual under treatment, but timed to provide maximum benefit with respect to improved glucose management. An alternative approach is to establish group objectives within a peer community and encourage collaborative achievement of those objectives (e.g. participation in a large scale physical activity event for charity)'.

Clinical Support Feedback

Identified clinical support teams will be provided feedback as permitted by the user on general patterns of activity, glycaemia and through email, text, social media and the internet. This information will be used to reinforce positive behaviour change. The identified others will also be able to provide feedback and support through these media. This information may be used to provide tailored and/or automated support messages.

ALGORITHMS AND ADDITIONAL EXAMPLES

Figure 6:
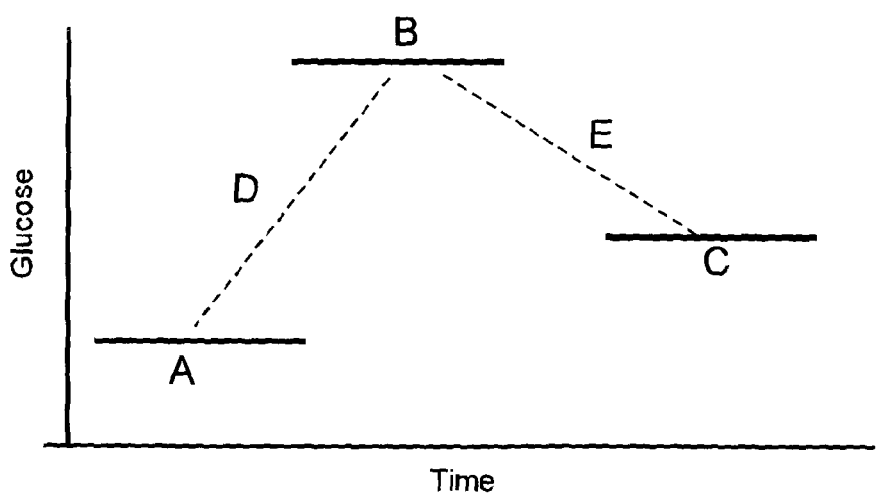
FIG. 6 shows an exemplary core system algorithm for continuously evaluating current glucose level in relation to an ideal glucose level.
Figure 7:
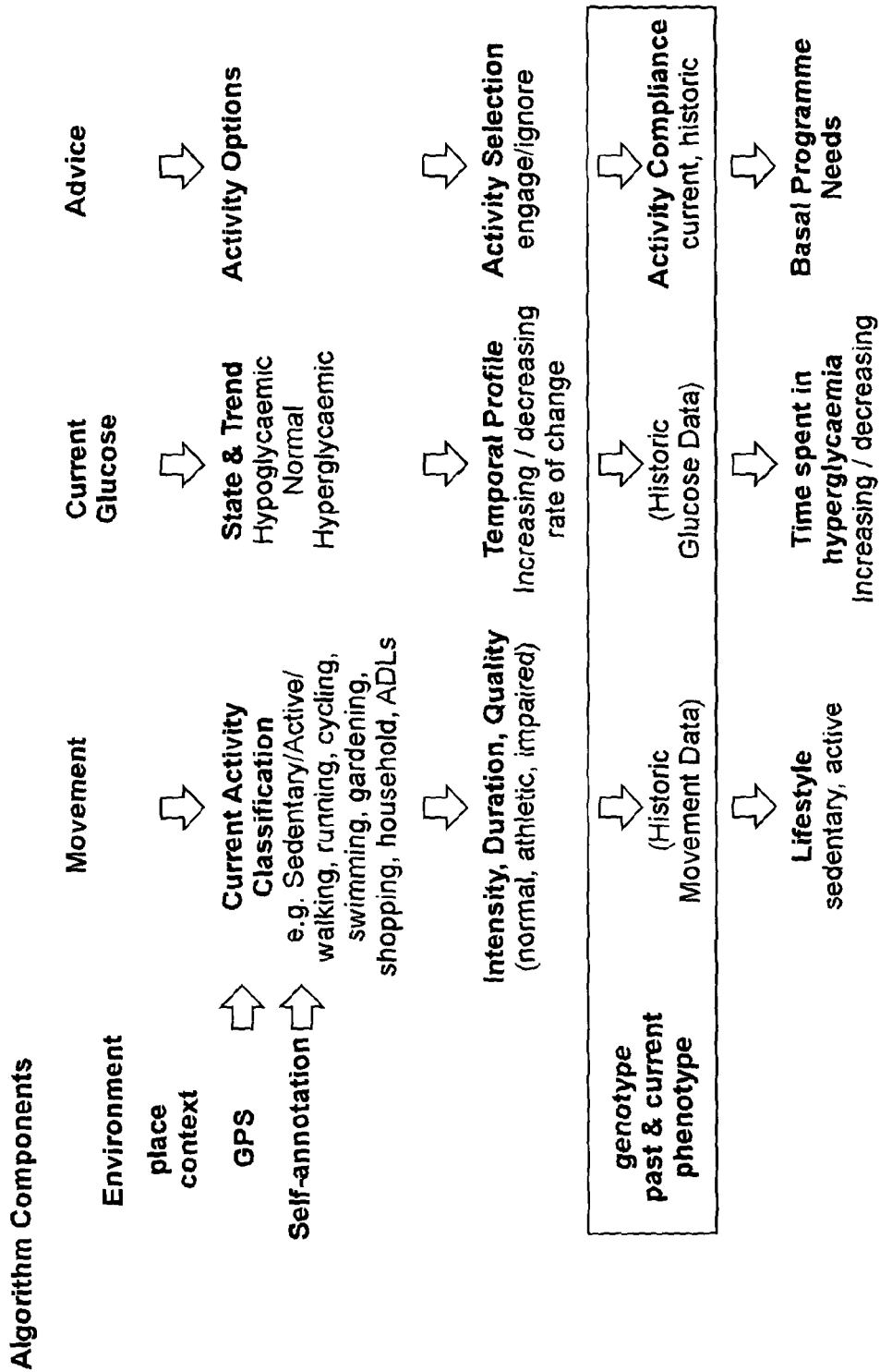
FIG. 7 shows further details of the components of the algorithm of FIG. 6.

The core system algorithm, as shown in FIG. 6, continuously evaluates the current glucose level in relation to the ideal glucose level. The algorithm may suggest or guide the individual to a self-identified target glucose level that accommodates the known rate of change expected from that individual in their current physiological condition for specific activities which are compatible with the individual capability and other relevant psychological and environmental factors that may promote or limit attainment (FIG. 7).

The core algorithm aims to adjust the frequency and content of prompts to improve underlying glucose disposal capability and maximise the likelihood of compliance to immediate prompts for physical activity in response to elevating/elevated plasma glucose directed at minimising the periods spent in hyperglycemia.

Example Individual A

Individual A with Type 2 diabetes for two years is male, Asian, non-smoker, no alcohol, aged 46 and has a BMI of 28: 5 ft 8 in, 184 lbs (83.4 kg), treated for high blood pressure and for elevated cholesterol but no history of MI. Employed in professional occupation with long, irregular hours involving long distance travel with consequent irregular time shifts. Wife and three children, aged 8 to 14 years.

Initially, individual A suffers from severe extended nocturnal hyperglycemia in response to evening meal with family. The system identifies this characteristic as the primary target as daytime hyperglycaemic episodes are less severe. System responds by recommending evening brisk walk for 30 minutes with option of combined moderate for run 10 minutes. In addition, the system proposes basal improvement programme.

Individual A is highly compliant with walking recommendations and also engages in run. This is detected by movement sensor and positive glucose response evident.

From time to time, domestic or work related commitments interfere with compliance. System encourages some 'catch up' in subsequent week by extending duration of evening activity by 15 minutes and Individual A responds positively with further reduction in time spent in hyperglycemia.

Individual A responds to basal improvement recommendations suggesting planning one hour exercise sessions at gym one evening each week, combined with a weekend run, starting with 10 minutes and rising to 30 minutes over a 12 week period (adding these sessions to mobile based diary integrated into system also allows further validation of compliance to planned schedule as detected by movement sensors and glucose response).

Individual A complies and sessions are again recorded by movement sensor with positive effect on glucose clearance. As the basal glucose disposal improves further reductions of hyperglycaemic episodes results.

Periodic long distance flights disrupt sleeping pattern and impair glucose disposal and compliance with basal programme. This is detected by sensors and acute response recommendations increase. In addition, there is increased prompting for short episodes of movement in response to the sedentary periods associated with travel.

Movement sensors detect long periods of sedentary behaviour during normal working hours associated with hyperglycaemia and responds by regular, discrete prompts to initiate brief episodes of physical activity. Individual A responds positively and day time hyperglycaemic episodes are also reduced.

With continued high compliance and marked reductions in hyperglycaemic periods, the system continues to ramp up basal exercise level and acute response. Work and domestic demands start to limit compliance and recommendations stabilise to high compliance level with much improved glucose control. Positive messaging of progress and review of results via mobile media engender sustained behaviour change. Individual A shares data with wife and family.

Over time, Individual A observes faster glucose clearance which sustains adherence.

The system recommends exploration of active family pursuits at weekend as part of basal improvement. Individual A responds and records these in mobile diary. System detects glucose improvements and movement increase.

With combined dietary restraint, individual A achieves normal nocturnal glucose and evening acute response prompts no longer ramp up recommendations. Day time glucose control also achieved.

Example Individual B

Individual B, recently diagnosed with Type 2 diabetes is female, European in origin, non-smoker, occasional moderate alcohol, aged 55 and has a BMI of 36: 5 ft 2 in, 197 lbs (89.3 kg), normotensive, treated for elevated cholesterol and diuretics for right sided heart failure with fluid retention on lower limbs. Employed as rotating shift worker with long sedentary periods during normal working hours. Teenage children and non-diabetic, overweight husband. Not engaged in recreational exercise/physical activity. Suffers from disturbed sleep. Finds sustained physical activity difficult due to existing condition.

On first use, individual B is suffers from chronic hyperglycemia and is rarely in normal range. There is a poor diurnal pattern with episodes of extended movement at night reflecting poor sleep and need to empty bladder. Individual C shows very low levels of physical activity, travelling to work by car and spending long periods during the day highly sedentary.

The system identifies primary need to disrupt sedentary periods by short, manageable episode of walking together with improved sleep hygiene.

The movement sensors detect slow, high BMI gait and attenuates activity recommendations to likely manageable levels.

Individual B responds to discrete daytime prompts to break up sedentary periods during the day but does not respond to prompts for light walking for 15 minutes each evening.

System recognises some increased activity associated with mid day and starts to recommend additional light walking for 15 minutes at this time. Individual B responds positively but associated acute glucose response with this detected activity deteriorates. The system identifies likely cause as associated snacking linked to the period of activity and alerts Individual B accordingly. Individual B responds positively and acute glucose response immediately improves.

Sudden shift pattern change is detected by system via movement sensors (most active and least active periods shift according to work pattern) and this is accompanied by further hyperglycaemic periods within three days of shift change.

System recognises movement issues for Individual B and recommends resistance exercise to improve muscle mass and armchair based upper body exercises. Individual B responds and slow improvements in hyperglycaemia.

Recognising poor evening compliance and shift disruption, system focuses on mid-shift, rather than mid-day, activity increase and secures improved compliance allowing gentle increase in physical activity from 10 minutes (complied walking period) to 20 minutes.

Episodic deterioration of movement due to fluid retention consequences reduces compliance. System promotes awareness of links to Individual b's care team to improve management and care. Over subsequent three months, individual b experiences improved mobility, recognised by consistent increased compliance with prompts to break up sedentary periods and to engage in mid shift activity. With clinical support team, individual B seeks change to normal work pattern away from shift work. This brings clear improvement in glucose control and significant reduction in time spent in hyperglycaemia. Clinical team also alerted to poor sleep and address sleep apnoea and nocturnal disruption caused by diuretics. Clinical team and Individual B observe further clear improvements in glucose control and reduced time in hyperglycaemia.

Example Individual C

Individual C, diagnosed T2 diabetes for over 15 years, male, european, ex-smoker, occasional moderate alcohol, aged 69 years has BMI of 26: 5 ft 10 in, 181 lbs (82.1 kg): Retired from manual employment with non-diabetic, normal weight/BMI spouse. Has already engaged in lifestyle behaviour improvement to achieve weight loss and enjoys walking and gardening. Reports generally good sleeping but tendency to wake and rise early.

On first use, movement sensors identify extended daytime sedentary behaviour but recognises physical activity associated with afternoon walking or gardening. Some mornings show elevated movement patterns associated with shopping with Thursday mornings especially consistent.

Individual C exhibits daytime hyperglycaemic excursions associated with midday meal but small evening meal limits nocturnal hyperglycaemia.

System identifies priority of breaking up extended sedentary periods in mornings and evenings and generates discrete prompts to breakup these periods with brief walking episodes combined with extended 30 minute walk before midday meal, except following active mornings, such as the Thursday morning shop. System prompts opportunity to engage in running. Individual C complies well with discrete prompts to break up sedentary periods in morning and engages in walk but not run. This is detected by movement sensors. Prompts to engage in running are consistently ignored and Individual decides to silence running prompts after a few days. so system focuses on increasing period and intensity of walking episodes, extending to one hour pre mid-day meal walk at elevated walking speed.

Response to evening prompts remains poor. System prompts opportunity for alternative activities in evenings and individual C identifies dancing classes with wife on Tuesday evenings. Movement sensors detect this and glucose disposal improvements result.

Over time, the reduced engagement in gardening through the winter months becomes evident with consequence of increased periods in hyperglycemia as a result. The movement sensors detect this seasonal reduction in movement and consequence on glucose clearance and substitutes prompts for increased walking episodes. Individual C complies with consequent benefits. As seasons revert, walking compliance reduces to be replaced by voluntary gardening activity and walking prompts are moderated due to sustained glucose control from substituted activity at normal prompting times and no impairment of glucose control.

In summary, the invention relates to a system or device that includes apparatus to improve dysregulated metabolic control in a mammal through prompted episodes of physical activity comprising;

means of measuring a metabolically significant analyte (e.g. glucose in T2DM)

means of measuring movement of the body (e.g. MEMS accelerometer)

user-observable/discernible indicators to prompt episodes of physical activity (e.g. integrated LED or separate display such as mobile phone)

data storage means and a processing unit, programme and interface means to accept data from the means of measuring the metabolically significant analyte and body movement and independent means to control the start and finish of device operation.

data communication means (e.g. usb, wireless) to provide feedback either to user or other parties (e.g. clinical care team in case of T2DM)

A programme to immediately prompt and record physical activity in response to deteriorating metabolic control (e.g. absolute level indicative of, or upward trend in glucose likely to give rise to, hyperglycaemia in T2DM)

The system or device may incorporate additional programme capability to prompt and record physical activity based on extent and level of metabolic dysregulation (e.g. period spent in hyperglycaemia) and associated patterns of physical activity/movement previously recorded.

It is envisaged that the system could be integrated into lifestyle management programme combining dietary and physical activity recommendations

The invention claimed is:

1. A system for regulation of blood glucose, the system comprising:

a movement sensor;

a glucose monitor;

an output device for providing a signal to a subject;

a microcontroller having a memory associated therewith;

wherein the movement sensor is adapted to take and record real-time continuous or regular movement readings to determine movement of a subject;

wherein the glucose monitor is adapted to take and record continuous or semi-continuous real-time readings of levels of blood glucose present in the subject;

wherein the memory associated with the microcontroller stores historical readings from the movement sensor and the glucose monitor;

wherein the microcontroller compares real-time readings with recorded historical readings and determines a rate and a direction of change of the levels of blood glucose and associated levels of physical activity; and wherein the microcontroller recommends a type of physical activity dependent on 1) at least one of the rate and direction of change of the real time glucose level correlated with 2) a current activity level from the movement sensor, using the historical readings as a reference; and wherein the output device displays the recommended type of physical activity; and wherein the recommended type of physical activity is monitored in real time using the movement sensor and an effect of the recommended type of physical activity on the blood glucose is monitored in real time by the glucose monitor and feedback to adjust the recommended type of physical activity is given by the output device if at least one of the rate and change of blood glucose is determined by the microcontroller to not be within a predetermined range.

2. The system as in claim 1 wherein the system can also determine a measure of total movement or type of movement.

3. The system as in claim 1 comprising a clock.

4. The system as in claim 1 wherein movement and basal glucose levels over a set time period can be analysed by the microcontroller and target activity levels set for a forthcoming time period, wherein an activity program is based on analyzing the basal glucose levels and wherein the activity program facilitates improved basal glucose clearance by interrupting sedentary behavior.

5. The system as in claim 1 wherein the movement sensor comprises a pedometer.

6. The system as in claim 1 wherein the movement sensor comprises an accelerometer.

7. The system as in claim 1 wherein the movement sensor comprises an gyroscope.

8. The system as in claim 1 wherein the movement sensor is a MEMS based accelerometer.

9. The system as in claim 1 comprising at least one of temperature sensors and skin conductivity sensors.

10. The system as in claim 1 wherein the movement sensor is provided with means for associating the movement sensor with a body of the subject.

11. The system as in claim 1 wherein the glucose monitor is at least one of non-invasive and minimally invasive.

12. The system as in claim 1 wherein the physiological analyte sensor is a microneedle array based sensor.

13. The system as in claim 1 wherein physiological analyte sensor is an optical sensor.

14. The system as in claim 1 wherein the physiological analyte sensor is transdermal.

15. The system as in claim 1 wherein the output device comprises at least one of a visual, an audible, and a tactile output.

16. The system as in claim 1 wherein the output device comprises a viewing screen.

17. The system as in claim 1 wherein the output device comprises means for providing real time location information.

18. The system as in claim 17 wherein the means for providing real time location information is a global positioning system receiver.

19. The system of claim 1, wherein the glucose monitor takes samples at a frequency of approximately five minutes or less.

20. A method for the regulation of physiological analytes utilizing the system of claim 1 wherein:
- the movement sensor takes and records continuous or regular movement readings to determine movement of the subject;
- levels of one or more physiological analytes present in the subject are taken and recorded;
- readings are compared to recorded historical readings to determine a rate and a direction of change of the levels of one or more physiological analytes and associated levels of physical activity; and
- if the levels of one or more of the physiological analytes fit a certain profile a signal is sent to the subject.

21. The method as in claim 20 wherein multiple signals are available for selection for provision to the user and the signal provided to the user is selected depending on at least one of the rate and the direction of change of analyte levels.

22. The method as in claim 21 wherein multiple signals are available for selection for provision to the user and the signal provided to the user is selected to prompt a known activity which, in accordance with historical data, will direct analyte levels in a desired direction.

* * * * *